(12) United States Patent
Doidge et al.

(10) Patent No.: US 8,712,512 B2
(45) Date of Patent: Apr. 29, 2014

(54) APPARATUS AND METHOD FOR EXERTING FORCE ON A SUBJECT TISSUE

(75) Inventors: Mark S. Doidge, Toronto (CA); Joseph D. Mocanu, Toronto (CA)

(73) Assignee: Cerebral Diagnostics Canada Incorporated, Toronto (CA)

( * ) Notice: Subject to any disclaimer, the term of this patent is extended or adjusted under 35 U.S.C. 154(b) by 314 days.

(21) Appl. No.: 13/191,103

(22) Filed: Jul. 26, 2011

(65) Prior Publication Data

US 2012/0053483 A1 Mar. 1, 2012

Related U.S. Application Data (60) Provisional application No. 61/368,049, filed on Jul. 27, 2010.

(51) Int. Cl.
*A61B 5/04* (2006.01)
(52) U.S. Cl.
USPC ............................ 600/544; 600/300; 601/108
(58) Field of Classification Search
USPC .......................... 600/544, 545; 601/108, 1, 84
See application file for complete search history.

(56) References Cited

U.S. PATENT DOCUMENTS

| | | | |
|---|---|---|---|
| 4,467,815 A | 8/1984 | O'Brien et al. | |
| 5,002,065 A | 3/1991 | LaCourse et al. | |
| 5,022,407 A | 6/1991 | Horch et al. | |
| 5,191,896 A | 3/1993 | Gafni et al. | |
| 5,220,921 A | 6/1993 | Ferris et al. | |
| 5,230,345 A | 7/1993 | Curran et al. | |
| 5,363,859 A | 11/1994 | Tuckett et al. | |
| 5,381,805 A | 1/1995 | Tuckett et al. | |
| 5,433,211 A | 7/1995 | Brammer et al. | |
| 5,533,514 A | 7/1996 | Lavigne et al. | |
| 5,592,947 A | 1/1997 | Lavigne et al. | |
| 5,673,703 A | 10/1997 | Fisher et al. | |
| 6,702,756 B2 | 3/2004 | Brown | |
| 6,723,106 B1 | 4/2004 | Charles et al. | |
| 6,929,607 B2 | 8/2005 | Lipman | |
| 7,399,281 B2 | 7/2008 | Shimazu et al. | |
| 2006/0074354 A1* | 4/2006 | Barlow et al. | 600/590 |

OTHER PUBLICATIONS

Product Manuel entitled "Algometer", *Somedica Production Lab*, 2 pgs. (2004).

(Continued)

*Primary Examiner* — Navin Natnithithadha
*Assistant Examiner* — Etsub Berhanu
(74) *Attorney, Agent, or Firm* — Tarolli, Sundheim, Covell & Tummino LLP (57) ABSTRACT

An apparatus for exerting force on a subject tissue includes a linear motor for generating a force according to a predetermined force profile incorporating at least one motion control parameter. The linear motor is directly coupled to a motor output member to drivingly produce linear motion of the motor output member under direction of a motor controller executing the predetermined force profile. A tissue-contacting member is connected to the motor output member for directly proportional linear motion therewith. A load cell provides load cell feedback to the motor controller. The motor controller adjusts the motion of the motor output member responsive to the load cell feedback to substantially conform the motion to the predetermined force profile. The linear motor moves the tissue-contacting member to contact the subject tissue according to the predetermined force profile and responsively initiate a subject reaction to the exerted force.

56 Claims, 6 Drawing Sheets

(56) References Cited

OTHER PUBLICATIONS

Dagtekin et al., Measuring Pressure Pain Thresholds. Comparison of an Electromechanically Controlled Algometer with Established Methods, *Schmerz*, 21:439-444 (2007) (Attached is an English Abstract).
Webpage http://www.engineeringtalk.com/news/aer/aer118.html, entitled An Introduction to Linear Motors, pp. 1-4, with an indicated date of 2001.
Webpage http://www.designnews.com/article/9979-When_to_Chose_a_Linea . . . , entitled "When to Chose a Linear Motor", pp. 1-2, with an indicated date of 2006.
Pages i through 149 Thesis of Shuping Xiong, submitted to the faculty of The Hong Kong University of Science and Technology in Partial Fulfillment of the Requirements for the Degree of Doctor of Philosophy in Industrial Engineering and Engineering Management entitled "Pressure Perception on the Foot and the Mechanical Properties of Foot Tissue During Constrained Standing Among Chinese" (2008).
Pages 1 through 60 Thesis of Li Wang, submitted to the faculty of Laboratory for Cortical Plasticity and Human Brain Mapping, Center for Sensory Motor Interaction (SMI), Department of Health Science and Technology, Aalborg University, entitled "Brain Plasticity: Dynamic Changes of the Cerebral Activity as Effect of Pain Modulation" (2007).
MacDonald et al., "An Algometer for the Automated Measurement of Pain Threshold", *British Journal of Rheumatology*, 29:454-455 (1990).
Webpage printout from *Universal—Kumedikaru News*, partially translated, 2 pages, (undated).
Webpage printout from Somedic entitled "Electronic von Frey", 3 pages, with an indicated date of 2005.
Webpage printout from Somedic, entitled "Technical Specifications—Alogometer", 2 pages, no indicated date.
Harris et al., "Comparison of Clinical and Evoked Pain Measures in Fibromyalgia", *J. Pain* 7:521-527 (2006) (Abstract Only).
(Presumed) Presentation Abstract of Graven-Nielsen et al., entitled "Assessing Musculoskeletal Pain", 5 pages, with an indicated date of 1996.
Webpage www.eeconnet.com, entitled "Electronic Algometer", with an indicated date of 2006.
Manual for Algobase from Somedic Production AB, pp. 1-10 with an indicated date of 2011.
Excerpts from Garcia et al., entitled Gender Differences in Pain Threshold, pp. 568-572 and 574, with an indicated date of 2008.
System Overview entitled "PATHWAY Pathway Pain & Sensory Evaluation System", *Medoc Advanced Medical Systems*, Version 6, pp. 1-3, 6-15 with an indicated date of 2006.
Table of Contents with Abstracts, *Journal of Musculoskeletal Pain*, 6:1-6 (1998).
Garcia et al., "Gender Differences in Pressure Pain Threshold in a Repeated Measures Assessment", *Psychology, Health & Medicine*, 12:567-579 (2007) (Abstract Only).
Hoang et al., Abstract of paper appearing in "Engineering in Medicine and Biology Society", 1:403-406 (2004) (Abstract Only).
Bentley et al., "Source Localisation of 62-electrode Human Laser Pain Evoked Potential Data Using a Realistic Head Model" (2001) (Abstract Only).
Bentley et al., "Anatomical Localization and Intra-Subject Reproducibility of Laser Evoked Potential Source in Cingulate Cortex, Using a Realistic Head Model", *Clinical Neurophysiology*, 13:1351-1356 (2002) (Abstract Only).
Dowman, "Pain-Evoked Anterior Cingulate Activity Generating the Negative Difference Potential May Reflect Response Selection Processes", *Psychophysiology*, 39:369-379 (2002) (Abstract Only).
Webpage http://www.smi.auc.dk/docschool/2004/eegerpmp.pdf, entitled "Brain Plasticity: Dynamic Changes of the Cerebral Activity as Effect of Pain Modulation", 1 page, with an indicated date of 2004.
Excerpts from Debatisse et al., entitled "Pain Stimulation by Using Synchronised Somatosensory Evoked Potentials I(SSEPs) and Contact Heat Evoked Potentials (CHEPs)", No source available, with an indicated date of 2006.
Cooper et al., "A Stimulator for Studies of Mechanical Nociception Based Upon a Commercially Available Translation Table", *J. Neurosci Methods*, 47:199-204 (1993) (Abstract Only).
Webpage http://www.wagnerinstruments.com, labeled Digital Algometer, 3 pages, (undated).
Johnson et al., "An Inexpensive, Self-Assembly Pressure Algometer", *Anaesthesia*, 52:1365-2044 (1997) (Abstract Only).

* cited by examiner

APPARATUS AND METHOD FOR EXERTING FORCE ON A SUBJECT TISSUE

RELATED APPLICATION

This application claims priority from U.S. Provisional Application No. 61/368,049, filed Jul. 27, 2010, the subject matter of which is incorporated herein by reference.

TECHNICAL FIELD

The present invention relates to an apparatus and method for exerting force on a subject tissue and, more particularly, to an apparatus and method for exerting force on a subject tissue in a standardizable and/or reproducible manner.

BACKGROUND OF THE INVENTION

Pain is a major problem for individuals and for society. The scientific search for pain signals has been going for decades. Chronic pain is a common and often serious condition, and it reduces the ability of a person to function effectively and enjoy life. In extreme cases, living becomes unbearable for the patient. Chronic pain has been linked to stress, traumatic experiences, genetics, and environmental factors. The present lack of objective, affordable, and safe methods of testing for pain makes it difficult for many people to prove that their pain is in fact real. Without proof, they face many additional problems. For example, their pain may be doubted by employers, doctors, families, and insurance companies. The lack of objective tests for pain is a problem not only for the sufferer, but also for society in general. For example, adjudicators of accident cases lack tools to decide who to believe—when employees seek disability leave, employers have trouble knowing if they should be compassionate and flexible or firm, and doctors don't know if a request for analgesics is reasonable. However, even transient or short-term pain can provide significant challenges to a patient's quality of life.

There is a need for improved subjective and objective methods of measuring and classifying mechanical pain (i.e. pain induced by exertion of force upon the body). There is also a need for devices that can measure, test for, and research losses in the touch system of the body (the "somatosensory system"). ("Somatosensory" is used herein to indicate sensory activity having its origin elsewhere than in the special sense organs [e.g., eyes and ears] and conveying information about the state of the body proper and its immediate environment—examples of somatosensation include light touch sense, mechanical pressure sense of the skin and deep tissues, dynamic/moving touch sense, and vibration sense.) These losses are found in many common medical conditions, including various diseases called neuropathies.

Touch sensation includes several factors including: superficial mechanical touch (e.g., a cotton ball passed lightly over the skin), deep mechanical touch (e.g., a subject is pressed through superficial soft tissues hard enough to push on/near bone); the ability to feel any movement over the skin, the ability to identify letters and shapes traced upon the skin, and the ability to sense vibration. Numerous diseases are known to affect the touch system. Loss of sensation may be tested by looking for touch thresholds such as the minimum pressure needed so that the subject can feel that he or she is being touched at all.

Standardization of the applied force stimulus is particularly important for certain techniques of the objective testing of pain and touch. Without reproducible force-applied stimuli, it is very difficult to do accurate scientific research into pain and its associated disorders, or to diagnose or treat patients having certain types of pain and touch dysfunctions.

Existing automated somatosensory mechanical stimulators include algometers (which test for mechanical pain), which are inaccurate and fail to deliver a sufficiently standardizable applied-force stimulus and also cannot press as lightly as is desirable to test for the loss of touch.

SUMMARY OF THE INVENTION

In an embodiment of the present invention, an apparatus for exerting force on a subject tissue is described. A linear motor is provided for generating a force according to a predetermined force profile. The predetermined force profile incorporates at least one motion control parameter. The linear motor is directly coupled to a motor output member to drivingly produce linear motion of the motor output member under direction of a motor controller executing the predetermined force profile. A tissue-contacting member is connected to the motor output member for directly proportional linear motion therewith. A load cell is mechanically interposed between the motor output member and the tissue-contacting member. The load cell provides load cell feedback to the motor controller and the motor controller adjusts the motion of the motor output member responsive to the load cell feedback to substantially conform the motion to the predetermined force profile. The linear motor moves the tissue-contacting member to contact the subject tissue according to the predetermined force profile and responsively initiate a subject reaction to the exerted force.

In an embodiment of the present invention, a method for somatosensory interaction with a subject tissue is described. An apparatus is provided, comprising: a linear motor for generating a force according to a predetermined force profile, the predetermined force profile incorporating at least one motion control parameter, the linear motor being directly coupled to a motor output member to drivingly produce linear motion of the motor output member under direction of a motor controller executing the predetermined force profile, a tissue-contacting member connected to the motor output member for directly proportional linear motion therewith, and a load cell mechanically interposed between the motor output member and the tissue-contacting member. The subject tissue is positioned in a predetermined orientation with respect to the tissue-contacting member. The predetermined force profile is provided to the motor controller. The tissue-contacting member is driven into contact with the subject tissue to exert the force on the subject tissue. Load cell feedback is provided with the load cell to the motor controller responsive to contact between the tissue-contacting member and the subject tissue. The motion of the motor output member is adjusted responsive to the load cell feedback to substantially conform the motion to the predetermined force profile responsive to the load cell feedback. A subject reaction to the exerted force is initiated. The subject reaction to the exerted force is detected.

In an embodiment of the present invention, a force exertion system is described. A tissue-contacting member is provided for selectively contacting a subject tissue. A motor is provided for selectively driving the tissue-contacting member into linear motion with respect to the subject tissue to contact the subject tissue according to a predetermined force profile. A motor controller is provided for directing operation of the motor according to the predetermined force profile. A user interface is provided for generating the predetermined force profile responsive to a user selection of at least one of a force exertion objective and a motion control parameter. A subject monitoring system contributing to a detection of the subject reaction to the exerted force is provided. The predetermined force profile is chosen from a plurality of predetermined force profiles including options for at least one of pressure pain threshold detection, pressure discomfort threshold detection, light touch threshold detection, vibration sense threshold detection, mechanical pain tolerance threshold detection, mechanical pressure withdrawal threshold, mechanical allodynia detection, pin prick pain threshold detection, sensory-motor reflex threshold detection, facial grimace threshold detection, and withdrawal reflex detection. The subject monitoring system includes options for: monitoring of at least one of brain activity and nerve impulses of the subject, visually detecting a physical reaction of the subject, aurally detecting a physical reaction of the subject, and interacting with the subject for subjective monitoring.

BRIEF DESCRIPTION OF THE DRAWINGS

For a better understanding of the invention, reference may be made to the accompanying drawings, in which.

DESCRIPTION OF EMBODIMENTS

Figure 1:
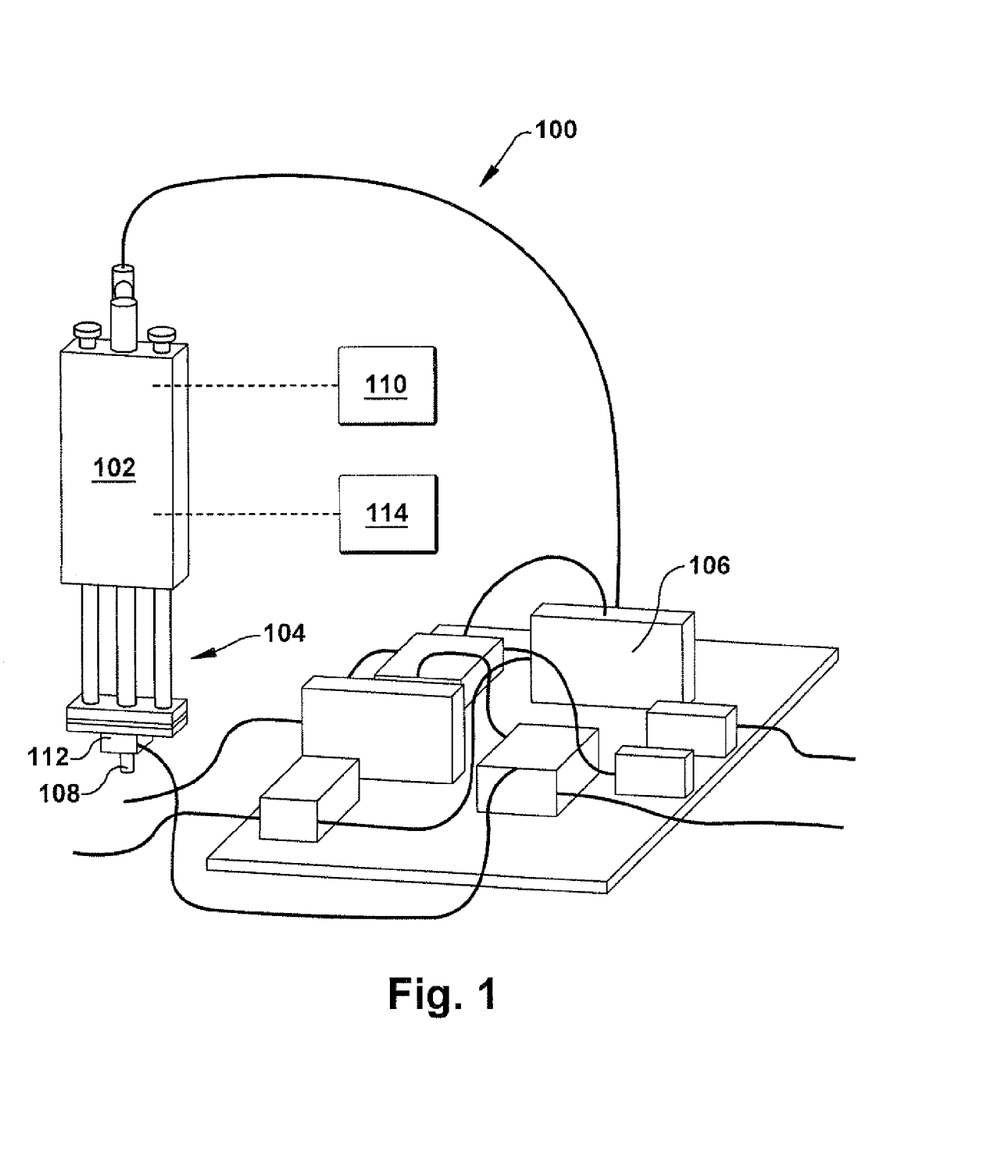
FIG. 1 is a schematic view of one embodiment of the present invention.

In accordance with the present invention, FIG. 1 depicts an apparatus 100 for exerting force on a subject tissue. The apparatus 100 can be used for mechanical somatosensory or somatomotor stimulation, or for any other desired purpose, some of which will be described in more detail below. ("Somatomotor" is used here to reference sensation pertaining to movements of the body.) The apparatus 100 includes a motor 102 for generating a force according to a predetermined force profile. The motor 102 may be directly coupled (i.e., without intervening structure) to a motor output member 104 to drivingly produce linear motion of the motor output member under direction of a motor controller 106 executing the predetermined force profile.

A linear motor may be used as the motor 102 for certain embodiments of the present invention. For certain applications of the present invention, linear motors may facilitate accurate control of linearly applied forces to the subject tissue in an economical, precise, efficient, repeatable, and easily programmed manner, including very fine-resolution control of the motor output member 104, that the inventors have not been able to achieve with current non-linear motor technology. The direct-linear-drive abilities of a linear motor may assist in simplifying the structure, assembly, and maintenance of the apparatus 100, as opposed to the use of a rotary-to-linear force converter with a rotary motor. In addition, the inventors have been surprised to learn that—unlike many motor devices—a linear motor can be used near an electroencephalogram ("EEG") machine without interfering with the EEG signal detection. One example of a suitable linear motor for use with certain embodiments of the present invention is the Linmot PS01-23x160-R stator with 44 N peak force output.

The motor 102 could also or instead be configured for usage near a magnetic resonance imaging ("MRI") machine. Because of the very large magnetic fields generated during MRI scanning, an apparatus 100 with metallic components may be difficult to use in a near-MRI environment. Accordingly, the motor 102 could be a pneumatic, non-metallic device. A motor 102 of any desirable type could also or instead be placed at a permissible "safe" distance away from the MRI machine, with an extension mechanism (not shown) such as, but not limited to, a sufficiently long motor output member 104 and/or a force transmitting device (e.g., a "push-pull" cable), made from a magnetically inert material and located between the motor and the patient tissue.

A tissue-contacting member 108 is connected to the motor output member 104 for directly proportional linear motion therewith. The configuration of the tissue-contacting member 108 is based upon the use of the apparatus 100; several example tissue-contacting members are described in conjunction with descriptions of example uses of the apparatus below. The motor 102, regardless of the type(s) selected or of any extension mechanisms present, moves the tissue-contacting member 108 to contact the subject tissue according to the predetermined force profile and responsively initiate a subject reaction to the exerted force.

The predetermined force profile is provided to the apparatus 100 by a user via a user interface 110. The user interface 110 is shown schematically (via dashed line) as providing instructions to the motor 102 in FIG. 1, but may be connected to any of the components of the apparatus 100 as desired to carry out the described control. The user interface 110, or any other suitable portion of the apparatus 110, could include a computer for generating the predetermined force profile responsive to a user selection of at least one of a force exertion objective and a motion control parameter. Example force exertion objectives include at least a chosen one of a somatosensory detection objective (stimulating at least one sense of the body, such as a light touch test), a somatomotor detection objective (stimulating at least one motor reflex of the body, such as a pain-flinch test), or any other desired objective for which a force is exerted on the subject tissue.

Optionally, a load cell 110 can be mechanically interposed between the motor output member 104 and the tissue-contacting member 108. When present, the load cell 110 may provide load cell feedback (which may encompass pressure, force, or any other suitable type of feedback) to the motor controller 106, and the motor controller 106 may then adjust the motion of the motor output member 104 at least partially responsive to the load cell feedback to substantially conform the motion of the tissue-contacting member 108 to the predetermined force profile. The load cell 110 may have any desired sensitivity for a particular application of the present invention. Additionally or alternatively, multiple load cells 110 could be provided and used, singly or in combination, as desired to produce appropriate load cell feedback. For example, the load cell 110 could be a first load cell 110, and a second load cell 110, selectively operative instead of the first load cell, could be similarly provided to the apparatus 100. In this situation, the second load cell 110 would be substantially more sensitive (i.e., "finer resolution") than the first load cell 110, and the second load cell can facilitate light touch threshold detection by providing second load cell feedback to the motor controller.

The apparatus 100 can be provided with any number of load cells 110, each having any desired resolution/sensitivity and being used in any desired sequence and/or combination during the use of the apparatus 100. For example, a relatively coarse-resolution load cell 110 could be a Transducer Technologies MLP-25 load cell with a 25-pound rating, and a relatively fine-resolution load cell 110 could be an Interface ULC-0.5N load cell for testing forces less than approximately 50 grams.

The tissue-contacting member 108 could be rigid or flexible, in whole or in part, and could have any desired configuration for a particular application of the present invention. For example, the tissue-contacting member 108 could present a blunt, substantially flat surface, having any desired dimensions, to the subject tissue. As another example, the tissue-contacting member 108 could present a pointed, needle-tip-like surface to the subject tissue (e.g., in carrying out pin prick testing). As another example, the tissue-contacting member 108 could include a textured material (e.g., sandpaper) to stimulate the skin in mechanical allodynia testing. As another example, the tissue-contacting member 108 could include a flexible portion (e.g., a monofilament similar to a Semmes-Weinstein tester), wherein a degree of bending of the tissue-contacting member when in contact with the subject tissue is associated with the exertion of a predetermined amount of force on the subject tissue—optionally, for use with this type of tissue-contacting member, the apparatus 100 could include an angle-measuring device or scale to facilitate determination of the degree of bending.

The apparatus 100 may include a subject monitoring system (shown schematically at 114 in FIG. 1) which contributes to a detection of the subject reaction to the exerted force. The subject monitoring system 114 may be subjective, semi-objective, and/or objective. A subjective test is one that relies entirely on the honesty and perception of the subject. An objective test is one that does not rely at all on the honesty of the subject—an example of an objective test includes the measurement of pain activity in a pain center of the brain. A semi-objective test is intermediate between an objective one and a subjective one and is believed to be difficult to fake by the subject.

As an example of a subjective subject monitoring system 114, the apparatus 100 could include a subject interaction interface (not shown) to subjectively detect the subject reaction to the exerted force, or any other desired self-rating tool used by a subject to indicate their reaction to a stimulus and/or how they perceive that the stimulus is affecting them. Suitable subject interaction interfaces could include interfaces such as, but not limited to, a pushbutton or release-button for the subject to activate in response to a particular degree of exerted force; an oral, signaled, or written indication to an observer of the subject's perception of the presence, absence, type, and/or degree of the exerted force (e.g., verbal rating scales [mild, moderate, severe, stabbing, burning], numerical rating scales ["0 to 10"], visual analogue scales [marking a point or moving a slider along a labeled line extending from "no pain" to "worst pain"], and the Wong-Baker FACES pain rating scale); movement of a body part (e.g., blinking eyes or lowering/raising a finger/hand to indicate sensation detection); and a non-verbal oral indication (e.g., a grunt or sigh).

An example of a semi-objective test is the measurement of fast and brief micro-expressions crossing the subject's facial features in response to a painful stimulus, or the distance or angle of movement of a limb as part of a reaction to pain. As an example of a semi-objective subject monitoring system 114, the apparatus 100 could include at least one of external visual observation and external aural observation of the subject to semi-objectively detect the subject reaction to the exerted force. For example, the subject could be video- and/or audio-taped during exertion of the force, and the tape reviewed (at full speed or otherwise) to detect indications of the subject's perception of the presence, absence, type, and/or degree of the exerted force. These indications could include, for example, the detection of micro-expressions (very brief facial expressions often lasting a fraction of second and which may be detected/measured with the help of tools such as the Facial Action Coding System (FACS) system developed by Ekman and colleagues or the Noldus Face Reading Program), bodily movements (e.g., a "kicking" of a foot after force is exerted to the knee, a withdrawal or "flinching" of a body part to which force is being applied—the apparatus 100 may be designed to quickly withdraw the tissue-contacting member 108 after exertion of force to avoid interfering with resulting bodily movements), and vocalizations (e.g., moans or groans). It is believed that certain of these types of indications are very difficult for a subject to produce intentionally, and therefore semi-objective subject monitoring can be useful in determining whether the exerted force is actually initiating the reaction or whether the subject may instead be intentionally or unintentionally falsifying his or her reaction to the exerted force.

To that end, it may be helpful for the external visual and/or aural observation to be correlated in time with the predetermined force profile. For example, a "beep track" (inaudible to the subject) giving an audible indication of changes in the exerted force according to the predetermined force profile could be provided to a video camera and recorded along with the visuals of the subject's reaction(s), so that an observer can decide if the subject's flinching occurred close enough in time to a change in the exerted force to likely be an involuntary and "true" reaction of the subject. If the time between the change in the exerted force and the subject's "involuntary" reaction is longer than expected, the observer may be able to hypothesize that the subject's reaction to the change in the exerted force was, in fact, intentional and may indicate a desire of the subject—for whatever reason—to mislead the observer as to the subject's true reaction to the exerted force.

As an example of an objective subject monitoring system 114, the apparatus 100 could include means for monitoring at least one of brain activity and nerve impulses of the subject and correlation of the monitored brain activity or nerve impulses of the subject to the predetermined force profile (using, perhaps, a more sophisticated version of the "beep track" just discussed) to objectively detect the subject reaction to the exerted force. Examples of suitable means for monitoring at least one of brain activity and nerve impulses of the subject include, but are not limited to, electroencephalography (EEG), evoked potentials/event-related potentials (ERP), evoked current densities (ECD—a derivative of EEG generated using multiple EEG electrodes and inverse solutions, which can be done with Dynamic Electrical Cortical Imaging—a software package that uses inverse solutions to display in 3D and to analyze and filter brain signals), magnetic resonance imaging (MRI), single photon emission computed tomography (SPECT), near-infrared spectroscopy (NIRS), positron emission tomography (PET), and magnetoencephalography (MEG). In addition to the means for monitoring at least one of brain activity and nerve impulses of the subject, the objective subject monitoring system 114 may include means for analyzing the signals (optionally using statistical analysis) produced by at least one of the brain activity and nerve impulses such as, but not limited to, independent component analysis (ICA), principal component analysis (PCA), event-related potential amplitude and latency measurements and analysis, event related current density of voxel analysis, frequency decomposition with Fourier transforms or windowed sync filters, event-related de-synchronization analysis, event-related synchronization analysis, power spectral analysis, and SPECTRE (a post-processing signal analysis system of current densities that automates calculation and display of mean current densities and of Poisson distributions, as described in currently pending International Application No. PCT/US2010/054282 [WIPO assigned PCT/IB2010/002973], filed Oct. 27, 2010, which claimed priority from U.S. Provisional Patent Application No. 61/255,120 and entitled "Spectral Decomposition and Display of Three-Dimensional Electrical Activity in the Cerebral Cortex").

Another technology that may be useful in analyzing brain activity and/or nerve impulses uses somatosensory evoked potential (SEP) and somatosensory evoked fields (SEF) analysis including the latencies and amplitudes of the various time points comprising the dataset. These are analyzed to make a diagnosis. The dataset may or may not include normal controls—for example, a light touch stimulus could serve as a baseline in patients suffering from the touch disorder of interest. It is possible to compare the averaged values of a patient's SEPs or SEFs to those in a normative database or a database of painful conditions. These databases could consist of SEPs generated in two states—pain state, and non-pain state (touch). The pain state data could be generated by stronger applications of force (often in the order of 40 N). Non-pain states could be generated by weaker applications of force (often less than 10 N).

Another technology that may be useful in analyzing brain activity and/or nerve impulses uses "single trial" analysis, which is analysis of solitary somatosensory waveforms generated using EEG or MEG in response to a somatosensory stimulus induced by the exerted force in order to discover features of interest and later extract these features from the brain data of an individual subject's response. This "single trial" analysis may be used for researching single stimulus events to determine normalcy or disease. Single trials can then be compared to normative and diseased data to draw diagnostic and physiological conclusions and, optionally, objectively test the subject for a disorder.

As an example of an objective monitoring system which may be carried out using a subject monitoring system 114 of the present invention, at least one of the brain activity and nerve impulses may be subjected to source localization using an inverse solution algorithm to localize the subject reaction to the exerted force. During this or any other type of signal analysis, the predetermined force profile may be correlated with the detected brain/nerve signals (analogously to the "beep track" which can be used with semi-objective testing) through association of one or more event markers (e.g., a "TTL" signal) with the detected brain/nerve signals, the event markers giving an indication of a change in the exerted force of the predetermined force profile (e.g., an application or release of an exerted force). Without correlation between the detected brain/nerve signals and the force exerted according to the predetermined force profile, it will be difficult for the user to achieve meaningful objective indications of the subject reaction of the exerted force.

As another example of an objective monitoring system which may be carried out using a subject monitoring system 114 of the present invention, the brain activity and/or nerve impulses of the subject may be monitored using EEG involving somatosensory evoked potentials to create averaged brain activity signals. A synchronization technology is used to create at least one event marker associated with the brain activity and/or nerve impulses at the time when the tissue-contacting member 108 contacts the subject tissue, and at least one of the averaged brain activity and/or nerve impulses and the event markers are analyzed using at least one brain signal analysis statistical tool or technology. Optionally, the averaged brain activity and/or nerve impulse signals may be compared to a library of normative brain activity and/or nerve impulse signals and/or diseased brain activity and/or nerve impulse signals in order to objectively test the subject for a disorder.

Using any of the described subject monitoring systems 114, or any other suitable method, the force exerted on the subject tissue by the apparatus 100 may be used for change monitoring (e.g., tracking the progression of a neuropathy), research, disease diagnosis, and/or disease treatment. For example, the apparatus 100 could be used with research into somatosensory as well as somatomotor disorder(s), including a number of known clinical mechanical pain phenomena such as, but not limited to, anesthesia, analgesia, hypoalgesia, central sensitization, spatial summation, temporal summation, wind-up, first pain, second pain, slow summation, neuropathic pain, hyperpathia, painful after-sensations, nociception, painful grimace threshold, allodynia, reactions to trigger point stimulation, reactions to tender point stimulation, reactions to control point stimulation, delayed onset muscle soreness (DOMS), and diffuse noxious inhibitory controls (DNIC). Other suitable research targets include, but are not limited to, somatomotor phenomena including deep tendon reflexes, withdrawal reflexes, and facial expression responses to painful stimulation.

Additionally, the force exerted on the subject tissue by the apparatus 100 may be used in at least one purpose related to the condition(s) of mechanical pain disorders, injuries/defects, and neuropathies. For example, the mechanical pain disorder could be at least one of fibromyalgia, temporo-mandibular joint disorder/dysfunction, chronic fatigue syndrome, myofascial pain syndrome, vulvar vestibulitis, pelvic tension mylagia, piriform is muscle syndrome, chronic widespread pain, Gulf War syndrome, reflex sympathetic dystrophy, complex regional pain syndrome, post-traumatic stress disorder, or other mechanical pain disorders. For example, the injury/defect could be at least one of joint damage, abnormal joint mechanics, sensitive tooth dental disorder, or other injuries/defects. For example, the neuropathy could be at least one of focal neuropathy, multi-focal neuropathy, toxic neuropathy, metabolic neuropathy, endocrine neuropathy, nutritional neuropathy, hereditary neuropathy, cranial neuropathy, psychological neuropathy, critical illness polyneuropathy, connective tissue neuropathy, neoplastic neuropathy, paraneoplastic neuropathy, infectious neuropathy, inflammatory neuropathy, demyelinating neuropathy, immune-related neuropathy, idiopathic neuropathy, hysterical hemi-anesthesia, diabetic neuropathy, or other neuropathies.

The apparatus 100 may be useful for purposes in addition to, or as subsets of, change monitoring, research, disease diagnosis, disease treatment, or the like, as well. As an example, the apparatus 100 could include a biofeedback treatment feature wherein a real-time (or near real-time) biofeedback indicative of their brain state may be offered to the subject and/or at least one of an incentive (reward) and a disincentive (punishment) could be selectively applied to the subject responsive to the subject reaction to the exerted force. (E.g., if the subject is a chronic pain patient with allodynia, thereby having exaggerated pain responses to ordinarily innocuous stimuli, it may be possible to train this person to have less abnormal brain responses with the help of the apparatus 100.)

As another example, the motor 102 may move the tissue-contacting member 108 to contact the subject tissue in order to move the subject tissue in a predetermined manner—in this scenario, the subject reaction is that the subject tissue is moved into a predetermined position. (E.g., imaging technologies could be used in a chiropractic use environment to identify a body part that requires repositioning, such as an intervertebral disc, and the apparatus 100 could press on the body in a predetermined manner to reposition the disk; an orthopedic fracture could be precisely reduced through the use of the apparatus.)

As another example, the motor 102 may move the tissue-contacting member 108 to contact the subject tissue in order to modify the subject tissue in a predetermined manner—in this scenario, the subject reaction is that the subject tissue is modified. (E.g., the accuracy and precision made possible by the apparatus 100 may be used to create surgical incisions or resections with a high degree of adherence to a presurgical plan.)

As another example, the motor 102 may move the tissue-contacting member 108 to contact the subject tissue in order to provide a predetermined therapeutic force to the subject tissue—in this scenario, the subject reaction is that the therapeutic force is applied in an effort to treat a disorder of the subject, (e.g., the apparatus 100 could be used to apply acupressure, acupuncture, therapeutic or relaxation massage, therapeutic vibration, or the like.)

Regardless of the purpose for which the apparatus 100 is being used, and the manner in which the subject reaction is detected, however, the apparatus 100 will generally be operated in a similar manner in most use environments, as will be discussed with reference to FIGS. 2-5B. The apparatus 100 can exert force upon the subject tissue via perpendicular motion, parallel motion, or any other suitable motion with respect thereto. For example, the tissue-contacting member 108 could be dragged across the surface of the subject tissue, could be lowered into point contact with the subject tissue, or could be applied in any other manner. For purposes of the below description, it will be presumed that the tissue-contacting member initially starts above the subject tissue and is then lowered perpendicular to the subject tissue until contact is made.

Figure 2:
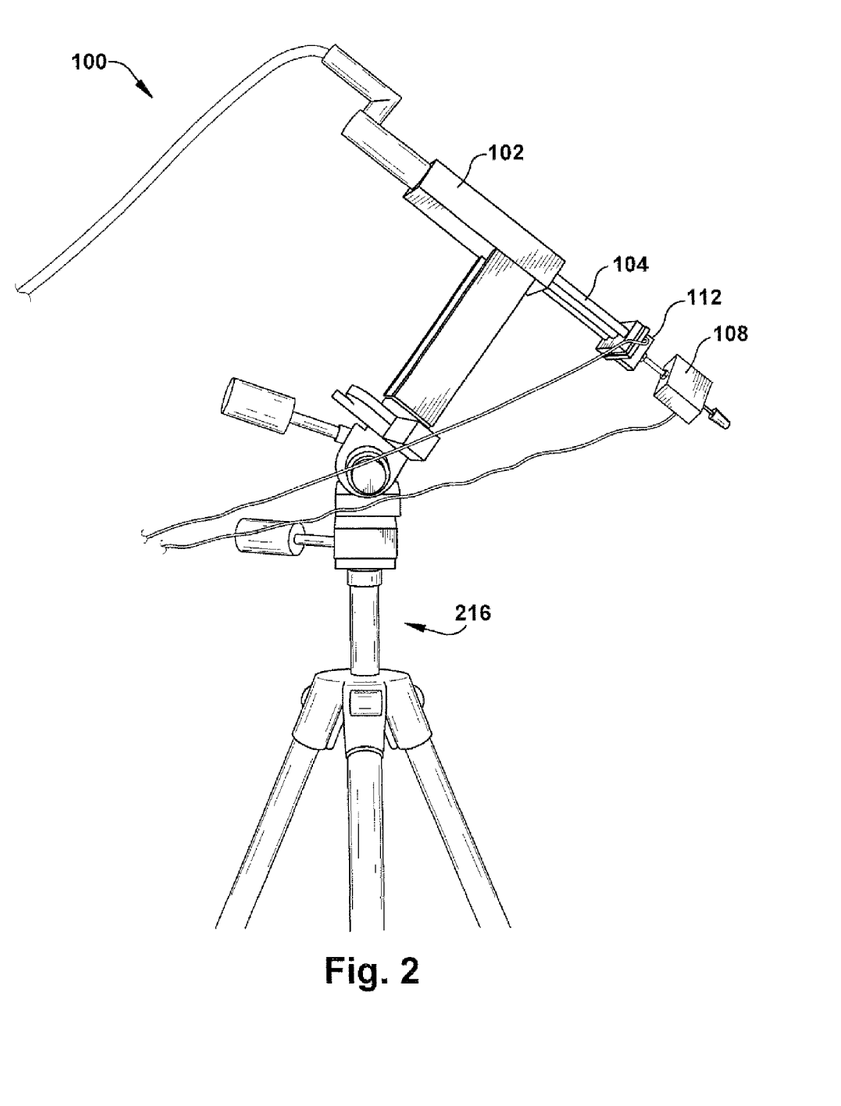
FIG. 2 is a partial side view of the embodiment of FIG. 1.

FIG. 2 is a partial side view of a portion of the apparatus 100 which includes a support structure 216. Here, the support structure 216 is a tripod stand, but the remaining components of the apparatus 100 could be supported by any type or number of support structure(s) or could be handheld by an operator, as desired for a particular application of the present invention. Optionally, the support structure 216 could be robotic/motorized or include some other automatic or manual "setting" means (not shown) to facilitate repeatable positioning of the tissue-contacting member 108 with respect to a subject tissue with the aim of providing reproducible exertion of force to the subject tissue over temporally spaced sessions with the apparatus 100.

Figure 3:
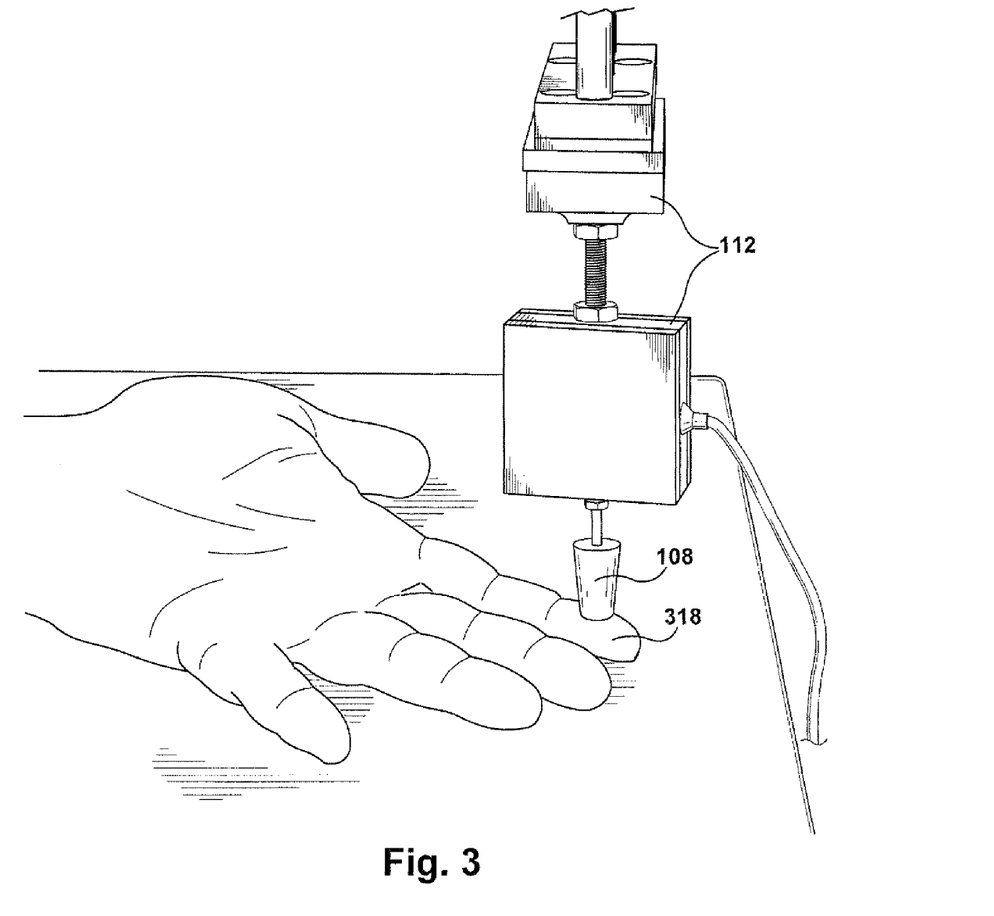
FIG. 3 is a partial side view of the embodiment of FIG. 2 in a first use environment.

FIG. 3 is a partial side view of the apparatus 100 configured to exert a force on a subject tissue 318 (here, a finger of a subject's hand). The apparatus 100 shown here includes two load cells 112, one coarse-resolution (upper, in the orientation of FIG. 3) and one fine-resolution (lower, in the orientation of FIG. 3)—these two load cells can be used together or separately as desired for a particular application of the present invention.

Once the subject tissue 318 has been arranged as desired with respect to the apparatus 100 and prepared for contact with the tissue-contacting member 108, the apparatus 100 can be actuated to carry out the predetermined force profile.

At any time before or during the operation of the apparatus 100, the predetermined force profile may be generated and/or selected by the user. (Though the predetermined force profile may be selected from a library of provided/possible predetermined force profiles, this description will use "generated" for simplicity in referring both to a selection of a previously generated custom or generic predetermined force profile and to custom-generation of a predetermined force profile based upon one or more contributing factors.) The predetermined force profile (a.k.a. "script") for a particular use instance of the present invention is contemplated to be generated responsive to a user selection of at least one of a force exertion objective and a motion control parameter.

As mentioned above, a force exertion objective may be any somatosensory and/or somatomotor detection objective—in other words, any objective for which force is being exerted by the apparatus 100. Examples of suitable force exertion objectives include, but are not limited to, at least one of pressure pain threshold detection, pressure discomfort threshold detection, light touch threshold detection, vibration sense threshold detection, mechanical pain tolerance threshold detection, mechanical pressure withdrawal threshold, mechanical allodynia detection, pin prick pain threshold detection, sensory-motor reflex threshold detection, facial grimace threshold detection, and withdrawal reflex detection.

A motion control parameter may be any contributing factor or parameter that goes into the generation of the predetermined force profile. Suitable motion control parameters include, but are not limited to, speed of travel of the tissue-contacting member 108, force (or pressure, hereafter presumed) exerted upon the subject tissue 318, duration of force exertion on the subject tissue, number of repetitions of force exertion on the subject tissue, "rest" (inter-stimulus) time period between exertions of force, and arrangement of desired force amounts/times into a desired exertion pattern (e.g., a smooth or "staircase" stepwise pattern of steadily escalating, steadily diminishing, or any other arrangement of different exerted forces as a routine to be carried out).

To aid the user in generating a predetermined force profile, a user-perceptible display may be provided to the apparatus 100, for example as a portion of the user interface 110. (A user input device, such as a touch screen, mouse, or other means for the user to communicate a choice to the apparatus 100 may also be provided.) Via the user-perceptible display, the user may be able to view a plurality of predetermined force profiles from a library and choose one of these previously generated predetermined force profiles.

The user-perceptible display may also or instead communicate information to a user regarding at least one of force, time, and distance of at least one predetermined force profile and, optionally, allow the user to generate (and possibly save for later use) a custom predetermined force profile. For example, the user-perceptible display may allow a user to input a desired peak force and ramp-up speed (or step length) for a predetermined force profile including a smooth (or stepwise) increase of exerted force. Another example of a user-generated predetermined force profile includes one for which the user specifies a force exertion amount and length of each exertion, rest period between force exertions, and total number of force exertions. One of ordinary skill in the art can readily provide any suitable predetermined force profile(s) for a desired application of the present invention.

Figure 4:
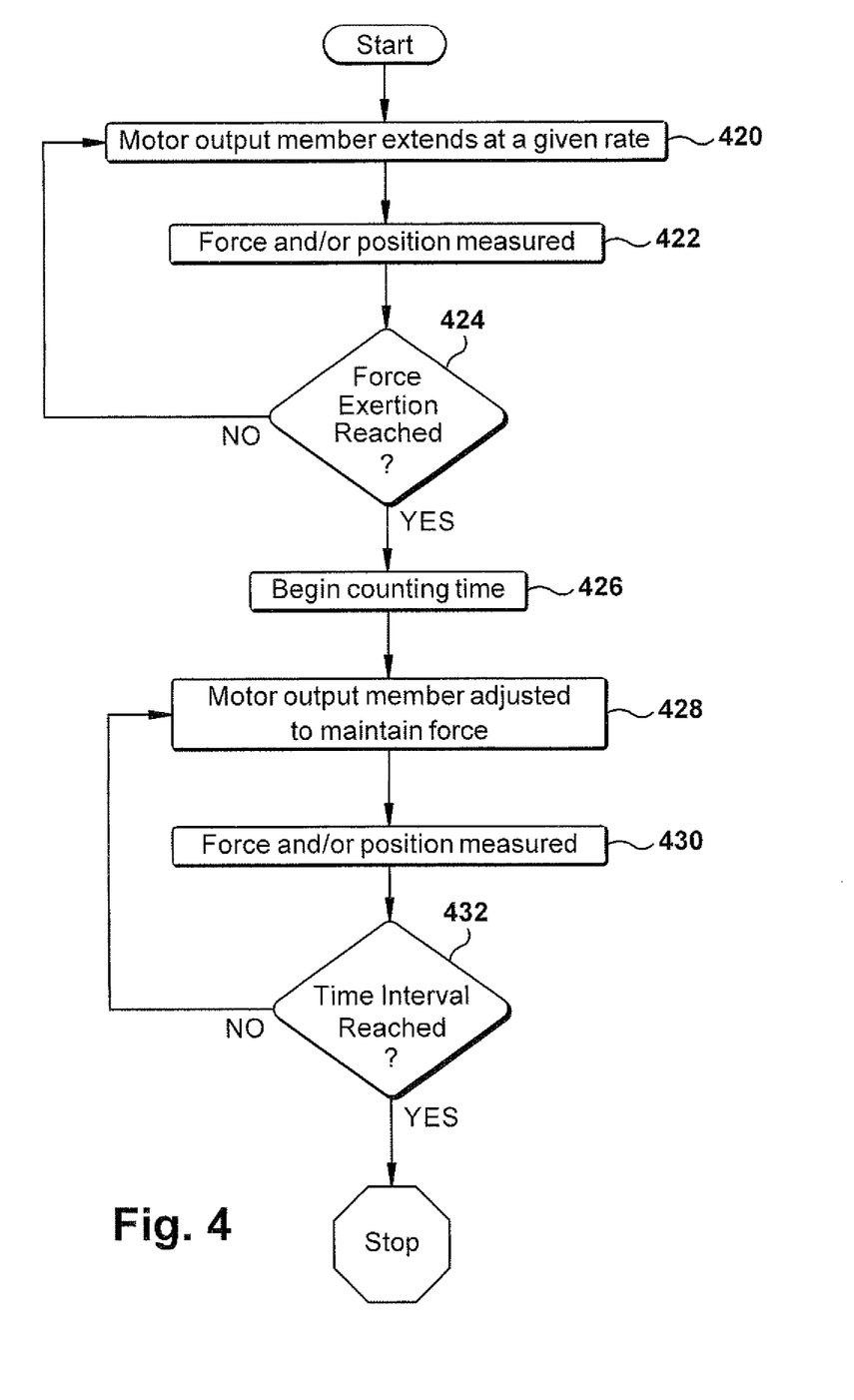
FIG. 4 is a flowchart depicting an example of a sequence of operation of the embodiment of FIG. 1.

Regardless of the manner in which the predetermined force profile is generated, it may be provided to at least a portion (e.g., the motor controller 106) of the apparatus 100, which then carries out the logic of the flowchart of FIG. 4. At first action block 420, the motor output member 104 is extended by the motor 102 at a predetermined rate (retraction or no extension are also encompassed in first action block 420, depending upon the nature of the force exertion being carried out). Control proceeds to second action block 422, where the force exerted and/or position of the tissue-contacting member 108 are measured (directly or indirectly). Force is measured by load cell 112 and position may be measured or calculated by the motor controller 106 or a sensor associated with the motor output member 104.

Control proceeds to first decision block 424, which determines whether the force exertion according to the predetermined force profile has been reached. This determination may be made with the help of load cell feedback. If the predetermined force profile has been reached, the motor output member 104 is held in position and control proceeds to third action block 426. If not, control returns to first action block 420 and the motor output member 104 continues to extend.

At third action block 426, the apparatus 100 maintains the tissue-contacting member 108 in contact with the subject tissue and begins counting time of the force exertion as dictated by the predetermined force profile and control proceeds to fourth action block 428. In fourth action block 428, the motor output member 104 is adjusted as desired to maintain the force exertion according to the predetermined force profile. Optionally, the load cell 112 feedback may be an input to fourth action block 428 to assist with conforming the actual exerted force to that planned in the predetermined force profile. At fifth action block 430, the force and/or position of the tissue-contacting member 108 are measured similarly to the second action block 422 measurements.

Control then proceeds to second decision block 432, at which the timing of force exertion is checked to see whether the force has been exerted for a time period conforming to the predetermined force profile. If so, then the operation terminates, optionally repeating for another segment of the predetermined force profile if the entire profile has not been carried out or if no user/subject stop has been instituted. If not, then control returns to fourth action block 428 and the motor output member 104 is adjusted as needed, and the logic continues as shown in FIG. 4. The logic of FIG. 4 may be repeated as many times as necessary to control the apparatus 100 and exert force upon the subject tissue 318 to carry out the entire predetermined force profile or a desired sub-portion thereof.

Figure 5A:
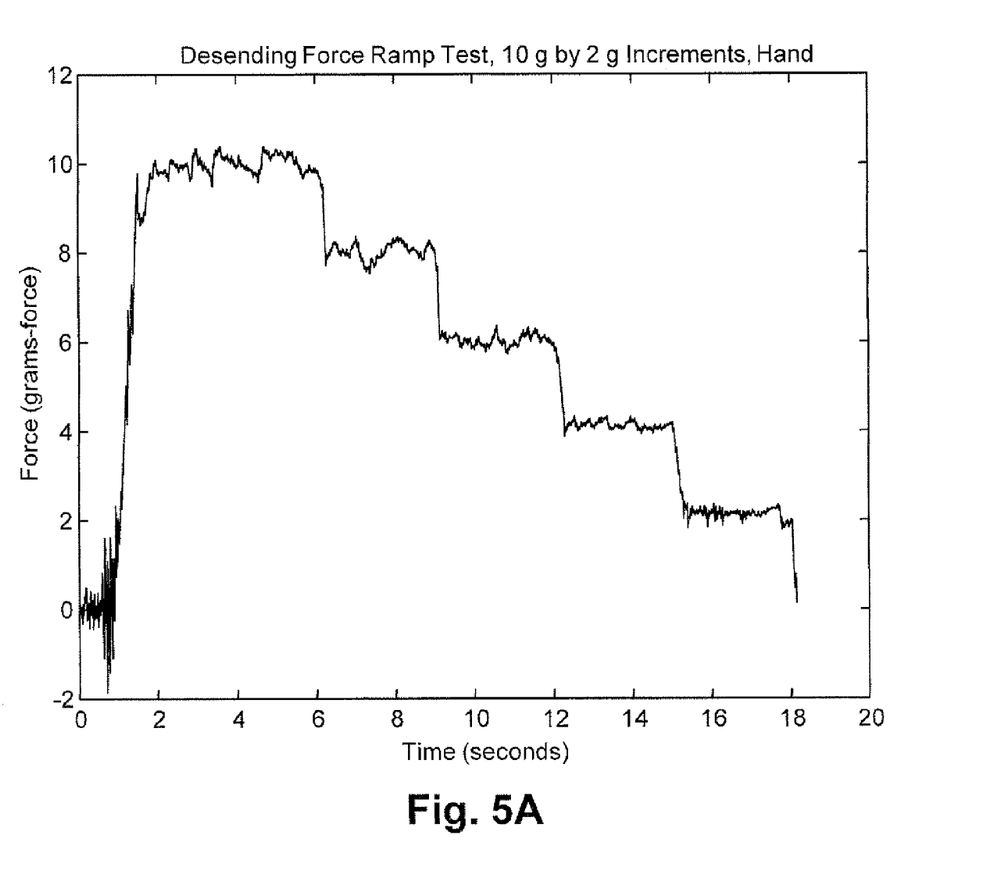
FIGS. 5A and 5B are graphs depicting example force applications of the embodiment of FIG. 1.
Figure 5B:
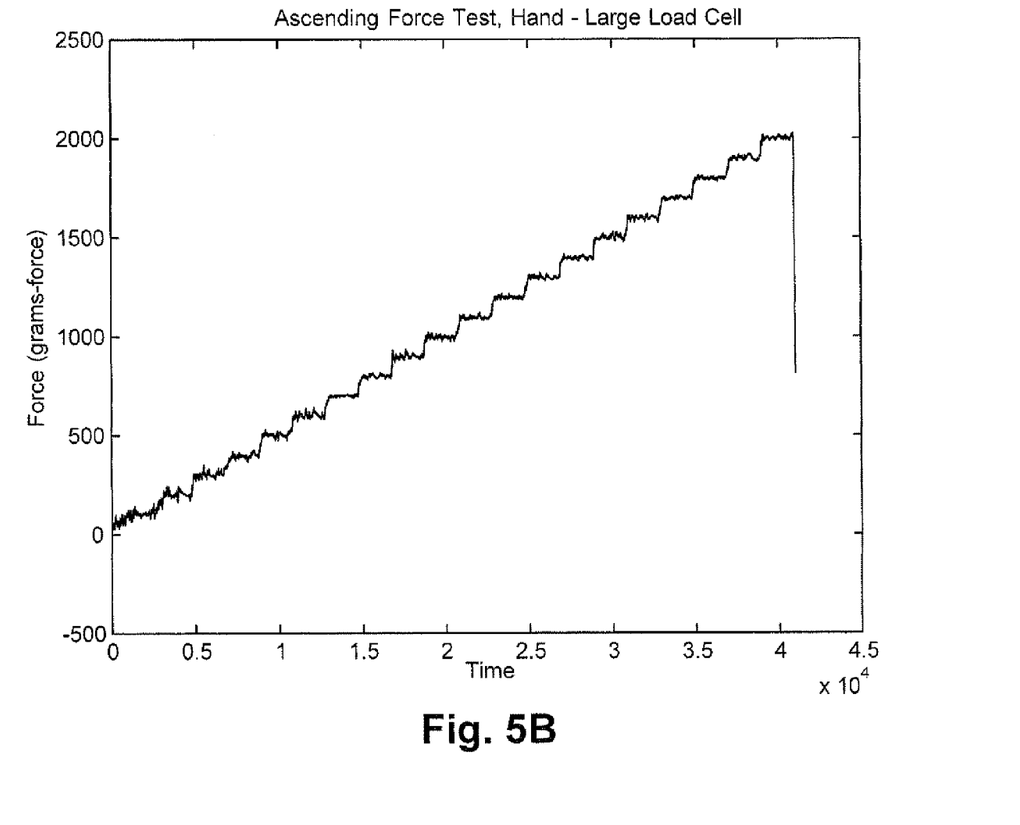

The apparatus 100 may also be configured to provide pre-, peri-, and/or post-force-exertion information regarding at least one of force, time, and distance to the user in a user-perceptible format. The graphs shown in FIGS. 5A-5B are illustrative of graphical depictions of predetermined force profiles which may reflect the actual force exerted on the subject tissue during one session with the apparatus 100. Optionally, information on subject reactions (e.g., divider lines when the subject activates a pushbutton or other subjective force-detection-information device) may also be included in a user-perceptible format and/or memorialized in a computer-accessible format. In this manner, records may be kept of the somatosensory or somatomotor characteristics of the subject across one or more sessions with the apparatus 100, for reasons including tracking progression of a disease, attempting to detect malingering or false reporting of pain/sensation, proving a genuine disorder to an employer or insurance company, collecting research data, or any other desired reason.

FIG. 5A is a force vs. time graph memorializing a stepwise descending ramp test according to a predetermined force profile carried out on a subject tissue 318. As can be seen by the relatively neat "staircase" formed in FIG. 5A, the motor controller 106 can adjust the motion of the motor output member 104 responsive to the load cell 112 feedback in a reasonably precise manner with substantially no force exertion overshoot, to substantially conform the actual force exerted to a predetermined force profile having at least one right-angle force adjustment (i.e., a "step" of the "staircase"). Similarly, FIG. 5B is a force vs. time graph memorializing a stepwise ascending ramp test according to a predetermined force profile carried out on a subject tissue 318, having smaller steps than the graph of FIG. 5A. As can be seen from the respective force values, FIG. 5A shows a relatively fine-resolution predetermined force profile and FIG. 5B shows a relatively coarse-resolution predetermined force profile.

An example embodiment of the apparatus 100 may have one or more operation characteristics that allow relatively precise control of force exertion compared to prior art devices, such as, but not limited to: application of force accurate to within 5 milliseconds; level of force applied accurate to within 0.056 Newtons using a 25 pound load cell and/or to about 11 grams using a 25 pound load cell, and possibly even more accurate with a 0.5 N load cell; speed at which force is applied ranging between 0.1 and 900 millimeters per second; position of the target movement of the slider accurate to within 0.1 millimeters, up to accuracy within one micron with the aid of a linear encoder; offering precisely timed repetitive stimulations so as to be able to perform evoked potential studies; precision of the 0.5 N load cell under ideal conditions in a low-noise environment estimated to be 41 milligram; and a self-adjusting feedback function which can used to allow the apparatus 100 to deliver a near constant controlled force to the body, regardless of the muscularity, size, and/or adiposity of the subject.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the described apparatus 100 are merely illustrative; one of ordinary skill in the art could readily determine any number of tools, sequences of steps, or other means/options for placing the above-described apparatus, or components thereof, into positions substantially similar to those shown and described herein. Any of the described structures and components could be integrally formed as a single piece or made up of separate sub-components, with either of these formations involving any suitable stock or bespoke components and/or any suitable material or combinations of materials. The user and/or subject may be provided with a "dead man switch", "emergency stop", or another means for halting the predetermined force profile before it has been completely carried out by the apparatus 100. Though certain components described herein are shown as having specific geometric shapes, all structures of the present invention may have any suitable shapes, sizes, configurations, relative relationships, cross-sectional areas, or any other physical characteristics as desirable for a particular application of the present invention. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. In addition to the described elements, any desired motive, sensing, controlling, monitoring, or other elements may be provided to the apparatus 100. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. An apparatus for exerting force on a subject tissue, the apparatus comprising:
   a linear motor for generating a force according to a predetermined force profile, the predetermined force profile incorporating at least one motion control parameter, the linear motor being directly coupled to a motor output member to drivingly produce linear motion of the motor output member under direction of a motor controller executing the predetermined force profile;
   a tissue-contacting member connected to the motor output member for directly proportional linear motion therewith;
   a load cell mechanically interposed between the motor output member and the tissue-contacting member;
   a computer for generating the predetermined force profile responsive to a user selection of at least one of a force exertion objective and a motion control parameter; and
   wherein the load cell provides load cell feedback to the motor controller and the motor controller adjusts the motion of the motor output member responsive to the load cell feedback to substantially conform the motion to the predetermined force profile; and
   wherein the linear motor is configured to move the tissue-contacting member to contact the subject tissue according to the predetermined force profile and responsively initiate a subject reaction to the exerted force.

2. The apparatus of claim 1, wherein the force exertion objective is a chosen one of a somatosensory detection objective and a somatomotor detection objective.

3. The apparatus of claim 1, including a subject monitoring system, the subject monitoring system contributing to a detection of the subject reaction to the exerted force.

4. The apparatus of claim 3, wherein the subject monitoring system includes means for monitoring at least one of brain activity and nerve impulses of the subject and means for correlating the monitored brain activity or nerve impulses of the subject to the predetermined force profile to objectively detect the subject reaction to the exerted force.

5. The apparatus of claim 4, wherein the brain activity of the subject is subjected to source localization using a computer running an inverse solution algorithm to localize the subject reaction to the exerted force.

6. The apparatus of claim 5, wherein the monitored brain activity is compared by the computer to a library of at least one of normative brain activity signals and diseased brain activity signals to objectively test the subject for a disorder.

7. The apparatus of claim 4, wherein the brain activity of the subject is monitored using electroencephalography means involving somatosensory evoked potentials to create averaged brain activity signals, a synchronization technology is used to create at least one event marker associated with the brain activity at the time when the tissue-contacting member contacts the subject tissue, and at least one of the averaged brain activity signals and the event markers are analyzed using at least one brain signal analysis statistical tool.

8. The apparatus of claim 7, wherein the brain activity of the subject is monitored using electroencephalography means involving somatosensory evoked potentials to create averaged brain activity signals, and the averaged brain activity signals are compared by the computer to a library of at least one of normative brain activity signals and diseased brain activity signals to objectively test the subject for a disorder.

9. The apparatus of claim 3, wherein the subject monitoring system includes at least one of external visual observation and external aural observation of the subject to semi-objectively detect the subject reaction to the exerted force.

10. The apparatus of claim 3, wherein the subject monitoring system includes a subject interaction interface to subjectively detect the subject reaction to the exerted force.

11. The apparatus of claim 1, wherein the load cell is a first load cell, and the apparatus includes a second load cell selectively operative instead of the first load cell, the second load cell being substantially more sensitive than the first load cell, the second load cell facilitating light touch threshold detection by providing second load cell feedback to the motor controller.

12. The apparatus of claim 1, wherein the motor controller adjusts the motion of the motor output member responsive to the load cell feedback to substantially conform to a predetermined force profile having at least one right-angle force adjustment with substantially no force exertion overshoot.

13. The apparatus of claim 1, wherein the tissue-contacting member is rigid.

14. The apparatus of claim 1, wherein at least a portion of the tissue-contacting member is flexible, and wherein a degree of bending of the tissue-contacting member when in contact with the subject tissue is associated with the exertion of a predetermined amount of force on the subject tissue.

15. The apparatus of claim 1, including a biofeedback treatment feature wherein at least one of the following occurs: a substantially real-time biofeedback indicative of their brain state is offered to the subject, an incentive is selectively applied to the subject responsive to the subject reaction to the exerted force, and a disincentive is selectively supplied to the subject responsive to the subject reaction to the exerted force.

16. The apparatus of claim 1, wherein the linear motor is configured to move the tissue-contacting member to contact the subject tissue in order to move the subject tissue in a predetermined manner, and the initiated subject reaction is that the subject tissue is moved into a predetermined position.

17. The apparatus of claim 1, wherein the linear motor is configured to move the tissue-contacting member to contact the subject tissue in order to modify the subject tissue in a predetermined manner, and the initiated subject reaction is that the subject tissue is modified.

18. The apparatus of claim 1, wherein the linear motor is configured to move the tissue-contacting member to contact the subject tissue in order to provide a predetermined therapeutic force to the subject tissue, and the initiated subject reaction is that the therapeutic force is applied in an effort to treat a disorder of the subject.

19. The apparatus of claim 1, including a user-perceptible display for communicating information to a user regarding at least one of force, time, and distance of the predetermined force profile.

20. A method for somatosensory interaction with a subject tissue, the method comprising the steps of:
   providing an apparatus comprising:
      a linear motor for generating a force according to a predetermined force profile, the predetermined force profile incorporating at least one motion control parameter, the linear motor being directly coupled to a motor output member to drivingly produce linear motion of the motor output member under direction of a motor controller executing the predetermined force profile,
      a tissue-contacting member connected to the motor output member for directly proportional linear motion therewith, and
      a load cell mechanically interposed between the motor output member and the tissue-contacting member;
   positioning the subject tissue in a predetermined orientation with respect to the tissue-contacting member;

generating the predetermined force profile responsive to a user selection of at least one of a force exertion objective and a motion control parameter;

providing the predetermined force profile to the motor controller;

driving the tissue-contacting member into contact with the subject tissue to exert the force on the subject tissue;

providing load cell feedback with the load cell to the motor controller responsive to contact between the tissue-contacting member and the subject tissue;

adjusting the motion of the motor output member responsive to the load cell feedback to substantially conform the motion to the predetermined force profile responsive to the load cell feedback;

initiating a subject reaction to the exerted force; and detecting the subject reaction to the exerted force.

21. The method of claim 20, wherein the force exertion objective is a chosen one of a somatosensory detection objective and a somatomotor detection objective.

22. The method of claim 20, wherein the step of detecting the subject reaction to the exerted force includes the steps of:

monitoring at least one of brain activity and nerve impulses of the subject; and correlating the monitored brain activity or impulses of the subject to the predetermined force profile to objectively detect the subject reaction to the exerted force.

23. The method of claim 22, wherein the step of monitoring at least one of brain activity and nerve impulses of the subject includes the step of monitoring brain activity of the subject using electroencephalography involving somatosensory evoked potentials to create averaged brain activity signals; and wherein the step of correlating the monitored brain activity or impulses of the subject to the predetermined force profile includes the steps of:

creating at least one event marker associated with the brain activity at the time when the tissue-contacting member contacts the subject tissue using a synchronization technology; and analyzing at least one of the averaged brain activity signals and the event markers using at least one brain signal analysis statistical tool.

24. The method of claim 23, including the step of comparing the averaged brain activity signals to a library of at least one of normative brain activity signals and diseased brain activity signals to objectively test the subject for a disorder.

25. The method of claim 22, wherein the step of correlating the monitored brain activity or impulses of the subject to the predetermined force profile includes the step of subjecting the monitored brain activity of the subject to source localization using an inverse solution algorithm to localize the subject reaction to the exerted force.

26. The method of claim 25, wherein the monitored brain activity is compared to a library of at least one of normative brain activity signals and diseased brain activity signals to objectively test the subject for a disorder.

27. The method of claim 20, wherein the step of detecting the subject reaction to the exerted force includes the step of at least one of externally visually observing and externally aurally observing the subject to semi-objectively detect the subject reaction to the exerted force.

28. The method of claim 20, wherein the step of detecting the subject reaction to the exerted force includes the step of providing a subject interaction interface to subjectively detect the subject reaction to the exerted force.

29. The method of claim 20, including the step of adjusting the motion of the motor output member responsive to the load cell feedback to substantially conform to a predetermined force profile having at least one right-angle force adjustment with substantially no force exertion overshoot.

30. The method of claim 20, wherein the tissue-contacting member is rigid.

31. The method of claim 20, wherein at least a portion of the tissue-contacting member is flexible, and including the step of associating a degree of bending of the tissue-contacting member when in contact with the subject tissue with the exertion of a predetermined amount of force on the subject tissue.

32. The method of claim 20, including the step of selectively supplying at least one of: substantially real-time biofeedback indicative of their brain state to the subject, an incentive to the subject responsive to the subject reaction to the exerted force and a disincentive to the subject responsive to the subject reaction to the exerted force.

33. The method of claim 20, wherein the step of driving the tissue-contacting member into contact with the subject tissue to exert the force on the subject tissue includes the step of moving the tissue-contacting member to contact the subject tissue in order to move the subject tissue in a predetermined manner; and wherein the step of initiating a subject reaction to the exerted force includes the step of moving the subject tissue into a predetermined position.

34. The method of claim 20, wherein the step of driving the tissue-contacting member into contact with the subject tissue to exert the force on the subject tissue includes the step of moving the tissue-contacting member to contact the subject tissue in order to modify the subject tissue in a predetermined manner; and wherein the step of initiating a subject reaction to the exerted force includes the step of modifying the subject tissue.

35. The method of claim 20, wherein the step of driving the tissue-contacting member into contact with the subject tissue to exert the force on the subject tissue includes the step of contacting the subject tissue in order to provide a predetermined therapeutic force to the subject tissue; and wherein the step of initiating a subject reaction to the exerted force includes the step of applying the therapeutic force in an effort to treat a disorder of the subject.

36. The method of claim 20, including the step of communicating information regarding at least one of force, time, and distance of the predetermined force profile in a user-perceptible format.

37. The method of claim 20, including the step of using the force exerted on the subject tissue for at least one purpose selected from the group consisting of: change monitoring, research, disease diagnosis, and disease treatment.

38. The method of claim 37, including the step of using the force exerted on the subject tissue in at least one purpose related to a condition selected from the group consisting of: mechanical pain disorders, injuries/defects, and neuropathies.

39. The method of claim 38, wherein the mechanical pain disorder is a chosen one of fibromyalgia, temporo-mandibular joint disorder/dysfunction, chronic fatigue syndrome, myofascial pain syndrome, vulvar vestibulitis, pelvic tension mylagia, piriformis muscle syndrome, chronic widespread pain, Gulf War syndrome, reflex sympathetic dystrophy, complex regional pain syndrome, and post-traumatic stress disorder;

the injury/defect is a chosen one of joint damage, abnormal joint mechanics, and sensitive tooth dental disorder; and the neuropathy is a chosen one of focal neuropathy, multifocal neuropathy, toxic neuropathy, metabolic neuropathy, endocrine neuropathy, nutritional neuropathy, hereditary neuropathy, cranial neuropathy, psychological neuropathy, critical illness polyneuropathy, connective tissue neuropathy, neoplastic neuropathy, paraneoplastic neuropathy, infectious neuropathy, inflammatory neuropathy, demyelinating neuropathy, immune-related neuropathy, idiopathic neuropathy, hysterical hemi-anesthesia, and diabetic neuropathy.

40. A force exertion system comprising:
a tissue-contacting member for selectively contacting a subject tissue;
a motor for selectively driving the tissue-contacting member into linear motion with respect to the subject tissue to contact the subject tissue according to a predetermined force profile;
a motor controller for directing operation of the motor according to the predetermined force profile;
a user interface for generating the predetermined force profile responsive to a user selection of at least one of a force exertion objective and a motion control parameter; and
a subject monitoring system contributing to a detection of the subject reaction to the exerted force; wherein
the predetermined force profile is chosen from a plurality of predetermined force profiles including options for at least one of pressure pain threshold detection, pressure discomfort threshold detection, light touch threshold detection, vibration sense threshold detection, mechanical pain tolerance threshold detection, mechanical pressure withdrawal threshold, mechanical allodynia detection, pin prick pain threshold detection, sensory-motor reflex threshold detection, facial grimace threshold detection, and withdrawal reflex detection ; and wherein
the subject monitoring system includes options for: monitoring of at least one of brain activity and nerve impulses of the subject, visually detecting a physical reaction of the subject, aurally detecting a physical reaction of the subject, and interacting with the subject for subjective monitoring.

41. The force exertion system of claim 40, including a load cell mechanically interposed between the linear motor and the tissue-contacting member, wherein the load cell provides load cell feedback to the motor controller and the motor controller adjusts the motion of the motor output member responsive to the load cell feedback to substantially conform the motion to the predetermined force profile.

42. The force exertion system of claim 41, wherein the motor controller adjusts the motion of the motor output member responsive to the load cell feedback to produce a force profile having at least one right-angle force adjustment with substantially no force exertion overshoot.

43. The force exertion system of claim 41, wherein the load cell is a first load cell, and the apparatus includes a second load cell selectively operative instead of the first load cell, the second load cell being substantially more sensitive than the first load cell, and the second load cell facilitating light touch threshold detection by providing second load cell feedback to the motor controller.

44. The force exertion system of claim 40, wherein the brain activity of the subject is monitored using electroencephalography means involving somatosensory evoked potentials to create averaged brain activity signals, a synchronization technology is used to create at least one event marker associated with the brain activity at the time when the tissue-contacting member contacts the subject tissue, and at least one of the averaged brain activity signals and the event markers are analyzed using at least one brain signal analysis statistical tool.

45. The force exertion system of claim 40, wherein the subject monitoring system includes means for correlation of the monitored brain activity or impulses of the subject to the predetermined force profile to objectively detect the subject reaction to the exerted force.

46. The force exertion system of claim 45, wherein the brain activity of the subject is monitored using electroencephalography means involving somatosensory evoked potentials to create averaged brain activity signals, and the averaged brain activity signals are compared to a library of at least one of normative brain activity signals and diseased brain activity signals to objectively test the subject for a disorder.

47. The force exertion system of claim 40, wherein brain activity of the subject is subjected to source localization using a computer running an inverse solution algorithm to localize the subject reaction to the exerted force.

48. The force exertion system of claim 47, wherein the monitored brain activity is compared by the computer to a library of at least one of normative brain activity signals and diseased brain activity signals to objectively test the subject for a disorder.

49. The force exertion system of claim 40, wherein the motor is a linear motor.

50. The force exertion system of claim 40, wherein the tissue-contacting member is rigid.

51. The force exertion system of claim 40, including a biofeedback treatment feature wherein at least one of the following occurs: a substantially real-time biofeedback indicative of their brain state is offered to the subject, an incentive is selectively applied to the subject responsive to the subject reaction to the exerted force, and a disincentive is selectively supplied to the subject responsive to the subject reaction to the exerted force.

52. The force exertion system of claim 40, wherein at least a portion of the tissue-contacting member is flexible, and wherein a degree of bending of the tissue-contacting member when in contact with the subject tissue is associated with the exertion of a predetermined amount of force on the subject tissue.

53. The force exertion system of claim 40, wherein the motor is configured to move the tissue-contacting member to contact the subject tissue in order to move the subject tissue in a predetermined manner, and the subject reaction is that the subject tissue is moved into a predetermined position.

54. The force exertion system of claim 40, wherein the motor is configured to move the tissue-contacting member to contact the subject tissue in order to modify the subject tissue in a predetermined manner, and the subject reaction is that the subject tissue is modified.

55. The force exertion system of claim 40, wherein the motor is configured to move the tissue-contacting member to contact the subject tissue in order to provide a predetermined therapeutic force to the subject tissue, and the subject reaction is that the therapeutic force is applied in an effort to treat a disorder of the subject.

56. The force exertion system of claim 40, including a user-perceptible display for communicating information to a user regarding at least one of force, time, and distance of the predetermined force profile.

* * * * *